United States Patent [19]

Kurihara et al.

[11] Patent Number: 5,164,483
[45] Date of Patent: Nov. 17, 1992

[54] γ-CARBOXYGLUTAMATE DERIVATIVE, METHOD FOR PREPARING THE SAME AND METHOD FOR PREPARING HUMAN OSTEOCALCIN USING THE SAME

[75] Inventors: Takashi Kurihara; Eiji Taniyama, both of Ibaraki; Sachio Hirose, Tokyo, all of Japan

[73] Assignee: Mitsubishi Petrochemical Co., Ltd., Tokyo, Japan

[21] Appl. No.: 575,639

[22] Filed: Aug. 31, 1990

[30] Foreign Application Priority Data

Aug. 31, 1989 [JP] Japan ................ 1-223203

[51] Int. Cl.⁵ .............. C07K 1/06; C07K 1/04; C07K 3/04; C07K 7/10
[52] U.S. Cl. .............. 530/335; 530/333; 530/334; 530/336
[58] Field of Search ........... 530/324, 334, 335, 336, 530/333; 562/573

[56] References Cited

U.S. PATENT DOCUMENTS

| | | | |
|---|---|---|---|
| 4,212,795 | 7/1980 | Hughes et al. | 530/307 |
| 4,410,506 | 10/1983 | Price et al. | 436/542 |
| 4,438,208 | 3/1984 | Deftos et al. | 530/324 |

FOREIGN PATENT DOCUMENTS 0287798 11/1988 Japan .

OTHER PUBLICATIONS

Poser et al., *J. Biol. Chem.* 255:8685-8691, Sep. 25, 1981.
Marki et al., *Helvetica Chimica Acta* 60:807-815, 1977.
Zee-Cheng et al., *Bioc. and Biophys. Res. Comm.* 94:1128-1132, Jun. 30, 1980.
Danishefsky et al., *J. Am. Chem. Soc.*, 101:4385-4386, Jul. 18, 1979.
Barany et al. "Solid-Phase Peptide Synthesis", pp. 1-255, in *The Peptides,* Gross et al., editors, 1980.
Biological Abstracts, vol. 87, 1989, abstract No. 122392, L. Simionescu et al., "Methods of Isolation and Purification of Bovine and Rat Osteocalcin".
Chemical Abstracts, vol. 112, No. 15, Apr. 9, 1990, p. 794, abstract No. 139828a.

*Primary Examiner*—Robert A. Wax
*Assistant Examiner*—Stephen Walsh
*Attorney, Agent, or Firm*—Oblon, Spivak, McClelland, Maier & Neustadt

[57] ABSTRACT

Gla¹⁷ human osteocalcin and Glu¹⁷ human osteocalcin or salts thereof are prepared by introducing γ-carboxyglutamic acid into the amino acid sequence of said osteocalcin by employing a protective L-γ-carboxyglutamic acid represented by the formula:

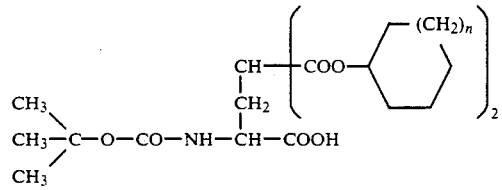

wherein n represents 0, 1 or 2, or a salt thereof in the appropriate position in the reacting sequence of amino acids which form the osteocalcin.

9 Claims, 4 Drawing Sheets

Y-CARBOXYGLUTAMATE DERIVATIVE, METHOD FOR PREPARING THE SAME AND METHOD FOR PREPARING HUMAN OSTEOCALCIN USING THE SAME

BACKGROUND OF THE INVENTION

This invention relates to a novel amino acid derivative, a method for preparing the same and a method for preparing human osteocalcin using the same which is an important index of bone metabolism and aging of human being.

Heretofore, as γ-carboxyglutamic acid derivatives as a starting material for chemical synthesis of partial fragment of a protein and a peptide, the following has been known.

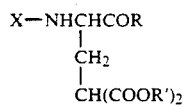

wherein X, R and R' each represent a combination as shown in the following table.

| Compound | X | R | R' |
|---|---|---|---|
| a | Cbz | $CH_3$ | tBu |
| b | Cbz | Bzl | tBu |
| c | Cbz | $CH_3$ | Bzl |
| d | tBoc | $CH_3$ | Bzl |
| e | Cbz | Phac | tBu | wherein Cbz represents a benzyloxycarbonyl group, tBu represents a t-butyl group, Bzl represents a benzyl group, tBoc represents a t-butyloxycarbonyl group and Phac represents a phenacyl group.

However, when the above compound is used as a starting material for the compounds shown in the above table, using the benzyloxycarbonyl (Cbzl) group as the α-amino protective group X is possible only in the case of the liquid phase method and it is not used or cannot be used (Compounds a, b, c and e) in the solid phase method or partial solid phase method. Also, regarding the compound d, when it is used in the solid phase method and in the partial solid phase method, a problem which exist is that selectively eliminating of only the α-carboxyl protective group R while leaving the protective groups R intact and R' is impossible.

The present inventors have found that in the above compound represented by the formula, a compound represented by the formula (I) mentioned below can be selectively deprotected for the above groups X, R and R' can be utilized in the solid phase method can be the partial solid phase method.

Osteocalcin (Bone Gla Protein: BGP) is a vitamin K dependent calcium bindable protein comprising 15 to 20% of the non-collagenic proteins of bone, and has been considered to be intimately related to both bone formation and bone absorption [Journal of Bone Metabolism Society of Japan 4, 56, 1986]. Poser et al analyzed the primary structure of human osteocalcin, and reported that human osteocalcin is a mixture of Glu[7] osteocalcin with the 17-position being glutamic acid and Gla[7] osteocalcin with the 17-position being γ-carboxyglutamic acid having the amino acid sequence shown below existing at a ratio of 91:9 [Poser, J. W. et al., Proc. Natl. Acad. Sci. U.S., 255, 8685-8691 (1980)].

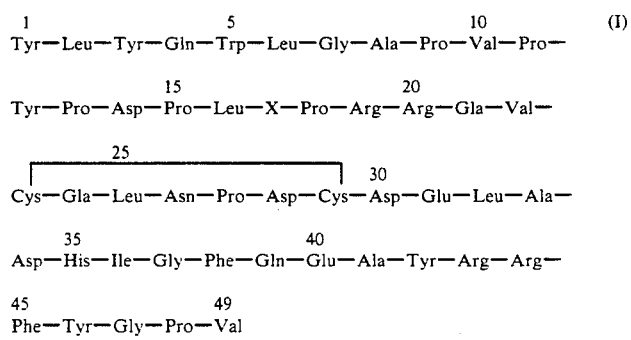

wherein X represents γ-carboxyglutamic acid residue (Gla) or glutamic acid residue (Glu).

However, osteocalcins of cattle, swordfish, cat, chicken, rat, goat, pig and rat already known up to date are all γ-carboxyglutamic acid at the corresponding site. As the reason, Poser et al estimate that calcified bone of aged people is used as the extraction material of human osteocalcin, and glutamic acid at the 17-position will change to γ-carboxyglutamic acid as man is older.

From such standpoint, establishment of human osteocalcin measuring system is not only clinically useful for diagnosis of bone diseases such as Paget's disease, bone metastasis, etc., but also can be expected to examine the relationship with aging by preparing the antibodies and antisera which recognize individually the 17-position Gla and Glu of human osteocalcin.

However, there exist none of measuring systems for quantitating separately Gla[7] human osteocalcin and Glu[7] human osteocalcin as a matter of course, and also human osteocalcin measuring system by use of human osteocalcin as the standard product. This is because Gla[7] human osteocalcin and Glu[7] human osteocalcin for specific antibody or antiserum preparation, and also as the standard product are not available.

In the present specification, the abbreviations, abbreviated symbols employed have the following meanings.

1 AMINO ACIDS

Ala: alanine, Arg: arginine, Asn: asparagine, Asp: aspartic acid, Cys: cysteine, Gla: γ-carboxyglutamic acid, Gln: glutamine, Glu: glutamic acid, Gly: glycine, His: histidine, Ile: isoleucine, Leu: leucine, Phe: phenylalanine, Pro: proline, Trp: tryptophan, Tyr: tyrosine and Val: valine.

In some cases, the respective abbreviations may show corresponding amino acid residues.

2. PROTECTIVE GROUPS

Boc: t-butyloxycarbonyl, Bu$^t$: t-butyl, Bzl: benzyl, OBzl: benzyl ester, OBu$^t$: t-butyl ester, OcHex: cyclohexylester, Br-Z: 2-bromobenzyloxycarbonyl, 4CH$_3$·Bzl: 4-methylbenzyl, Dnp: dinitrophenyl, MBzl: methoxybenzyl, Cl$_2$·Bzl: 2,6-dichlorobenzyl, Mtr:4-methoxy-2,3,6-trimethylbenzenesulfonyl, Mts: mesitylene-2-sulfonyl, Acm: acetamidomethyl, Tos: p-toluenesulfonyl, Fmoc: 9-fluorenylmethyloxycarbonyl, NO$_2$: nitro and HCO: formyl.

3. REAGENTS

DCC: dicyclohexylcarbodiimide, HOBt: 1-hydroxybenzotriazole, DTT: dithiothreitol, DCM: dichloromethane, DMF: dimethylformamide, MeOH: methanol, DIEA: diisopropylethylamine, THF: tetrahydrofuran, TFA: trifluoroacetic acid, HF: hydrogen fluoride, CH$_3$CN: acetonitrile, NMP: N-methylpyrrolidone and DMSO: dimethyl sulfoxide.

SUMMARY OF THE INVENTION

The present inventors have found a novel γ-carboxyglutamic acid derivative represented by the formula (XI) shown below which can be utilized for introduction of γ-carboxyglutamic acid in the peptide synthetic method.

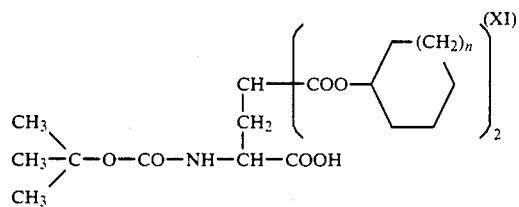

wherein n represents 0, 1 or 2.

The present invention also provides a method for preparing the γ-carboxyglutamic acid derivative represented by the formula (XI) and an optically active derivative thereof wherein its stereostructure at the side chain is L and an intermediate for producing said derivative.

The present inventors have also conducted intensive investigations into a method for synthesizing Gla$^7$ human osteocalcin by introducing Gla at the 17-position, the 21-position and the 24-position and have also prepared Glu$^7$ human osteocalcin according to chemical synthesis by introducing Gla at the 21-position and the 24-position, and consequently have accomplished the present invention.

The present invention is a method for preparing Gla$^7$ human osteocalcin and Glu$^7$ human osteocalcin or salts of these, which comprises introducing γ-carboxyglutamic acid in a peptide synthetic method of human osteocalcin by use of a protected optically active isomer (L isomer) of γ-carboxyglutamic acid represented by the above formula (XI) or a salt thereof.

DESCRIPTION OF THE PREFERRED EMBODIMENTS

Figure 1:
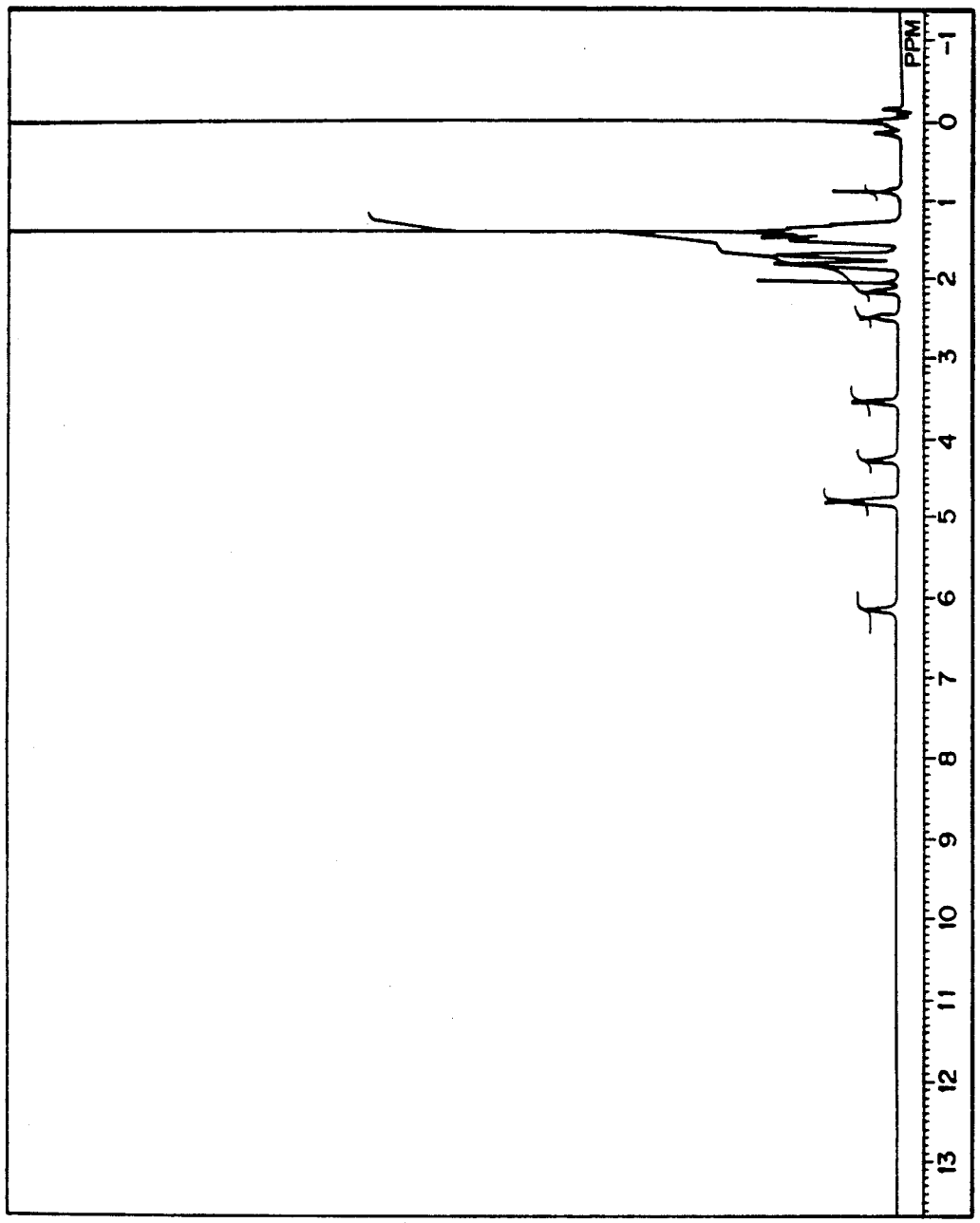
FIG. 1 is a chart showing the $^1$H-NMR spectrum of the optically active isomer (L isomer) of the compound (XI) obtained in Example 1.

Peptide synthesis can be performed by the liquid phase method or the solid phase method according to the methods described in, for example, Haruaki Yajima, Shunpei Sakakibara, edited by Biochemical Society of Japan, Course of Biological Experiments (I), "Chemistry of Proteins" vol. 4, published by Tokyo Kagaku Dojin (1977); and Nobuo Izumiya et al "Basis and Experiment of Peptide Synthesis", published by Maruzen K. K. (1985). As the synthetic method of the human osteocalcin of the present invention, the solid phase method is preferred.

In the following, the case of synthesizing the Gla$^7$ human osteocalcin and a salt thereof of the present invention according to the solid phase method is to be described.

First, the C-terminal amino acid of the desired human osteocalcin, namely Val is bound to an insoluble resin as the protected amino acid. The protected amino acid resin having such C-terminal protected amino acid bound to an insoluble resin is commercially available and can be used as such. Subsequently, following the amino acid sequence of the human osteocalcin, protected amino acids are successively bonded from the C-terminal side to obtain a protected peptide resin. As the insoluble resin, there may be employed any of those known in the field of art concerned, as exemplified by a chloromethyl resin, an oxymethyl resin, a 4-(oxymethyl)phenylacetamidomethyl resin, and these resins can be eliminatable with HF (hereinafter called "Pam" resin), etc.

The "protected amino acid" is an amino acid with its functional group being protected according to a known method, and various kinds of protected amino acids are commercially available. When synthesizing the human osteocalcin of the present invention, it is preferred to choose either one of the protected amino acids shown below. First, the protective group of α-amino group of amino acid is Boc or Fmoc. The protective group of guanidino group of Arg is Tos, NO$_2$, Mtr. The protective group of carboxyl group of Asp, Glu is Obzl, OBu$^t$, OcHex. The protective group of mercapto group of Cys is 4CH$_3$·Bzl, MBzl, Acm. The protective group of imidazolyl group of His is Tos, Dnp, Fmoc. The indolyl protective group of Trp is HCO or it may be also not protected. The protective group of hydroxyl group of Tyr is Br-Z, Cl$_2$·Bzl, Bzl, Bu$^t$, or it may be also not protected.

The respective protective groups are required to be chosen adequately depending on the synthetic conditions of the peptide.

Gla at the 17-position, the 21-position and the 24-position in the Gla$^7$ human osteocalcin and Gla at the 21-position and the 24-position in the Glu$^7$ human osteocalcin can be introduced as the protected Gla of the above formula (XI). Synthesis of this protected Gla can be carried out according to the following method.

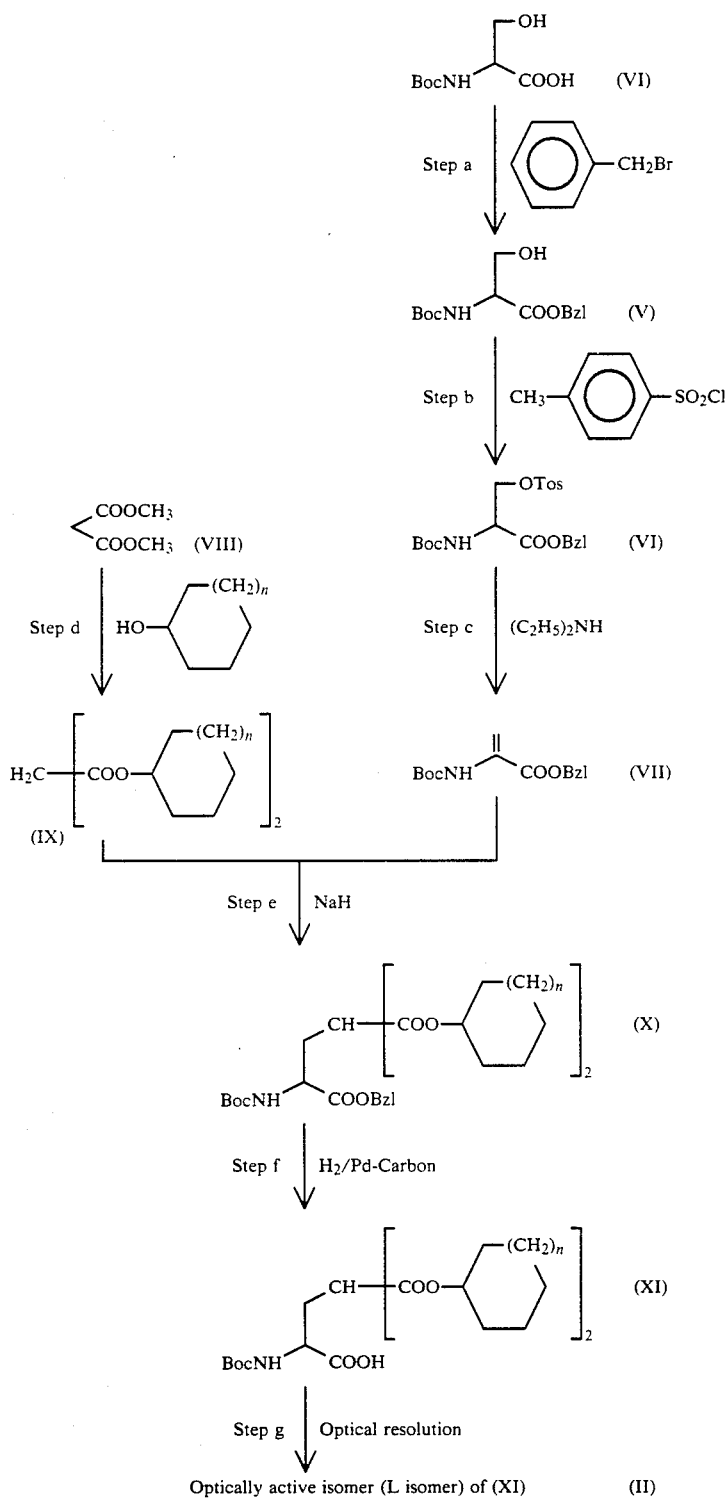

That is, first the reaction between N-t-butyloxycarbonylserine (IV) and a benzyl halide is carried out to synthesize a benzyl ester (V) (step a), then this is reacted with p-toluenesulfonyl chloride to form a sulfonate derivative (VI) (step b), which is reacted with a base such as diethylamine, etc. to synthesize N-t-butyloxycarbonyldehydroalaninebenzyl ester (VII) (step c).

On the other hand, by transesterification of dimethyl malonate (VIII), dicycloalkyl malonate (IX) is formed (step d). The compound (IX) is reacted with the compound (VII) obtained in the step c in the presence of sodium hydride as the base to synthesize a compound (X) (step e). Further, this is reduced to prepare a desired γ-carboxyglutamic acid derivative (XI) (step f). If desired, the compound (XI) obtained is optically resolved according to the diastereomer salt method by use an.

optical resolution agent such as quinine to prepare an optically active isomer (L isomer) (II) (step g).

The above step a can be practiced by adding benzylbromide and a base such as triethylamine, etc. into an acetone solution of t-butyloxycarbonylserine (IV) and heating the mixture at a temperature of room temperature to 100° C., preferably 40° C. to 70° C. for 5 hours or longer, preferably 20 to 60 hours. After completion of the reaction, the solvent is evaporated and the residue is poured into water, the product is extracted with ether and the solvent evaporated under reduced pressure to give the compound (V).

The step b can be practiced by dissolving the compound (V) obtained in the step a in a basic solvent such as pyridine, etc., adding p-toluenesulfonyl chloride to the solution and stirring the mixture at a temperature of $-20°$ C. to 40° C., preferably $-10°$ C. to 10° C. for 0.5 to 20 hours, preferably 2 to 8 hours. After completion of the reaction, the reaction mixture is added to cold water, followed by stirring, and the crystals formed are collected by filtration to give the compound (VI). Here, instead of the basic solvent, a base and a solvent such as triethylamine and THF, etc. can be used.

The step c can be practiced by dissolving the compound (VI) obtained in a mixed solution of ethyl acetate/diethyl ether, adding a base such as diethylamine, etc. to the solution and stirring the mixture at a temperature of $-20°$ C. to 40° C., preferably 0° C. to 30° C., for 0.5 to 20 hours, preferably 2 to 6 hours. After completion of the reaction, the reaction mixture is filtered and the solvent evaporated under reduced pressure to give the compound (VII).

The step d can be practiced by adding cycloalkanol and a catalyst such as p-toluenesulfonic acid into a toluene solution of dimethyl malonate (VIII) and stirring the mixture under heating at a temperature of 50° to 200° C., preferably 90° to 120° C., while evaporating methanol formed, for 5 hours or longer, preferably 20 to 60 hours. After completion of the reaction, the product is washed with a sodium hydrogen carbonate solution, the solvent evaporated under reduced pressure and then the residue is distilled to give the compound (IX).

The step e can be practiced by adding the compound (IX) into a suspension of sodium hydride in a solvent such as THF, stirring the mixture at a temperature of $-40°$ to 70° C., preferably $-10°$ to 40° C. for 0.1 to 10 hours, preferably 0.5 to 2 hours, subsequently adding dropwise a solution of the compound (VII) dissolved in the same solvent, and stirring the mixture at a temperature of $-40°$ to 70° C., preferably $-10°$ to 25° C., for 0.1 to 20 hours, preferably 0.5 to 10 hours. As the solvent which can be used here, in addition to THF, toluene, ethyl ether, dioxane, etc. can be included. After completion of the reaction, the compound (X) can be obtained according to conventional isolation and purification method such as extraction, column chromatography, etc.

The step f can be practiced by hydrolysis of the compound (X) obtained at a hydrogen pressure of 0.1 to 20 kg/cm$^2$, preferably 0.5 to 5 kg/cm$^2$, and at a temperature of 0° to 80° C., preferably 10° to 40° C. for 0.1 to 20 hours, preferably 0.5 to 10 hours, in the presence of a catalyst, in a solvent such as methanol or ethanol. As the reducing catalyst which can be used here, palladium-carbon, platinum-carbon, etc. can be included. After completion of the reaction, by separating the catalyst and evaporating the solvent under reduced pressure, the compound (XI) can be obtained.

The step g can be practiced by dissolving the compound (XI) in ethyl acetate, adding an optical resolution reagent to the solution and then repeating filtration and recrystallization with methanol. As the optical resolution reagent which can be used here, there can be included alkaloids such as quinine, brucine, cinchonidine, cinchonine, etc.; amines such as (R)-(+)-1-phenethylamine, (S)-(−)-1-phenethylamine, (R)-(+)-1-(1-naphthyl)ethylamine, (S)-(−)-1-(1-naphthyl)ethylamine, etc.; hydrazides such as tyrosine hydrazide, etc. After the reaction, the product is desalted and crystallized with n-hexane, followed by filtration, to give the optically active isomer (L isomer) (II) of the compound (XI).

The compound (XI) and its optically active isomer (II) thus obtained form salts with various inorganic bases and organic bases.

Examples of such salts can include alkali metal salts such as sodium salt, potassium salt, lithium salt; alkaline earth metals such as calcium salt, magnesium salt; organic base salts such as of methylamine, ethylamine, diethylamine, triethylamine, benzylamine, pyrrolidine, piperidine, cyclohexylamine, dicyclohexylamine, ethanolamine, diethanolamine, ornithine, lysine, arginine.

The above compound can be identified by its IR absorption, NMR spectrum and mass analysis. The optical purity of the optically active isomer can be determined by forming a diastereomer with an optically active base such as (+)-naphthylamine, (−)-naphthylethylamine, (+)-phenethylamine, (−)-phenethylamine, etc., separating this by conventional liquid chromatography and calculating the ratio of both substances. In this case, it is preferable to determine a correction coefficient according to the same operations also for the racemic mixture and correct the above optical purity by use thereof.

The configuration of the optically active γ-carboxyglutamic acid derivative of the present invention can be determined by hydrolyzing this substance in 0.1% phenol containing 6 N hydrochloric acid under reduced pressure at 110° C. for 22 hours to convert it to glutamic acid, and comparing the eluted position in high performance liquid chromatography of the reaction product of this with 2,3,4,6-tetra-O-acetyl-β-D-glucopyranosylisothiocyanate (hereinafter called GITC) according to the method of, for example, Futamura et al.[Journal of Chromatography, 316, 547-552 (1984)] with that of the reaction product of the standard L-glutamic acid, D-glutamic acid and GITC.

Protected amino acids can be bound according to conventional condensation methods such as the DCC method, the active ester method, the mixed or symmetric acid anhydride method, the carbonylimidazole method, the DCC-HOBt method, the diphenylphosphorylazide method, etc., of which the DCC method, the DCC-HOBt method, the symmetric acid anhydride method are preferred. These condensation reactions are carried out generally in an organic solvent such as DCM, DMF, NMP, chloroform, DMSO, benzene, etc. or a solvent mixture of them, but preferably in DCM, DMF or a solvent mixture of these. As the elimination reagent of the protective group of α-amino group, TFA/DCM, HCl/dioxane, piperidine/DMF, etc. may be employed, and may be chosen suitably depending on the kind of said protective group. The extent of progress of the condensation reactions in the respective steps of synthesis may be examined by the method of E.

Kaiser et al.[Anal. Biochem., 34, 595 (1970)] (Ninhydrin reaction method), etc.

Protected peptide resins having desired amino acid sequences are obtained as described above, and specific examples thereof are shown below.

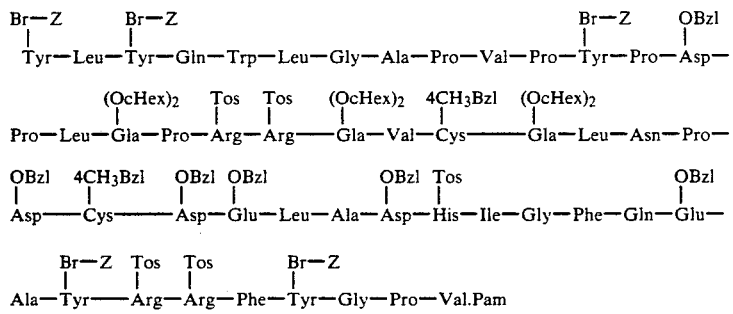

The protected peptide resin (Boc-Val-Pam resin) can be treated with a reagent which can eliminate the peptide from the resin and further eliminate side chain protective groups of the respective amino acids, for example, HF, TFA, etc. (final deprotection reaction) to give a peptide with mercapto group of Cys being deprotected.

By oxidizing the peptide in a buffer to form an intramolecular disulfide bond, the peptide can be obtained. More specifically, by dissolving the peptide with mercapto group of Cys being deprotected in a buffer to a concentration of $10^{-3}$ to $10^{-7}$ mole/liter, preferably $10^{-4}$ to $10^{-5}$ mole/liter, adjusting pH to 6.0 to 8.5, preferably 7.0 to 8.0, and then stirring the solution at 4° to 50° C., preferably 4° C. to room temperature for 4 to 30 hours, a crude human osteocalcin can be obtained. The buffer to be used in this reaction is known and may include, for example, ammonium acetate, Tris.HCl, etc. Also, as the promoting agent of this reaction, ferricyanate (potassium ferricyanate, etc.) can be added.

The crude human osteocalcin thus obtained can be purified by isolation by extraction, recrystallization, various chromatographic techniques (gel filtration, ion exchange, partition, adsorption, reverse phase), electrophoresis, countercurrent partition, etc., but the method according to reverse phase high performance liquid chromatography (reverse phase HPLC) is the most effective.

By utilizing human BGP ($Gla^{17}$ or $Glu^{17}$ human osteocalcin) according to the present invention, it can be realized to develop an immunological assay method of human BGP, and by effecting measurement of BGP in circulating blood, information for grasping condition of illness concerning bone metabolism can be obtained. That is, measurement of BGP in circulating blood of human has been carried out by an immunological assay method such as the radioimmunoassay (RIA) and the enzyme immunoassay (EIA) which utilize antiserum or a monoclonal antibody to bovine BGP or human BGP obtained from immunized rabbit, mouse or goat, but since a cross reaction with bovine BGP is utilized or a specific antibody is utilized for a fragment, these methods involve problems in measuring specificity, particularly measuring only intact molecule of 1 to 49, or measuring time and sensitivity should be improved.

Thus, an immunoradiometric assay (IRMA) which is specific to human BGP (1 to 49) can be accomplished by utilizing two monoclonal antibodies, in which one antibody is an anti-human BGP monoclonal antibody which is obtained by using the human BGP ($Gla^{17}$ and $Glu^{17}$ human osteocalcin) of the present invention as antigen and is specific to amino acid alignments at (12 to 33) of human BGP and the other antibody is an anti-bovine BGP monoclonal antibody which is specific to amino acid alignments at (30 to 49) of human BGP.

PREPARATION OF MONOCLONAL ANTIBODY PRODUCING HYBRIDOMA

Step a

PREPARATION OF ANTI-HUMAN BGP MONOCLONAL ANTIBODY PRODUCING HYBRIDOMA

The human BGP is a polypeptide comprising 49 amino acid residues and relatively low molecular weight, and thus it does not have sufficient immunogenicity. Accordingly, after it is combined with key-hole limpet hemocyanine, bovine serum albumin or swine thyroglobulin to prepare a composite material, the composite material is emulsified with a suitable immunoactivator such as a Freund's complete adjuvant to prepare an emulsion and the emulsion is injected into a mouse. The mouse to be used is generally a Balb/c species but any kind of mice which is normally used for immuniozation purposes can be used. Immunization can be carried out by repeatedly inoculating the abdomen of a mouse with the above emulsion by administration hypodermically several times for each several weeks. After 3 to 5 days from final immunization, the spleen is removed, and the spleen cells are adjusted and fused with a mouse myeloma cell (e,g, P3-X63-Ag8-U1, NS-1, X63-Ag8.653) to prepare a hybridoma. Cell fusion is carried out by the PEG method and screening of the fused strain is due to HAT selective medium. Screening for antibody production of the hybridoma is carried out by a known method such as EIA, RIA and the membrane fluorescent antibody technique whereby the hybridomas desired, which generate immunoglobulin specific to human BGP, are selected. Cloning of the hybridoma is carried out by the known method such as the limiting dilution method, or a method wherein while observing with a microscope, catching single cell with a glass capillary, etc.

Step b

PREPARATION ANTI-BOVINE MONOCLONAL ANTIBODY PRODUCING HYBRIDOMA

It can be carried out in accordance with the preparation of the monoclonal antibody producing hybridoma to human BGP.

Production of monoclonal antibody

Production of monoclonal antibody from the resulting hybridoma be carried out by two methods one of which is an in vitro system wherein the antibody is produced as a cultivated supernatant in a cultivating apparatus and the other of which is an in vivo wherein it is produced in the form of ascites in animal bodies such as abdominal cavity of mouse. In the in vitro system, the medium can be used by adding a suitable amount of bovine fetal serum to a usual Eagle's MEM, RPMI-1640 or Dulbecco's modified Eagle's medium. Cultivation period is generally 3 to 7 days. In the in vitro cultivation system, after inoculating hybridoma strains in abdominal cavity of mammal such as mouse, ascites is collected between 4 and 14 days to obtain monoclonal antibody as ascites. A large amount of monoclonal antibody can be obtained generally by the in vivo system.

The monoclonal antibody (ascites or cultivation supernatant) obtained by the above methods is subjected to purification by combining known methods such as salting out, DEAE-cellulose column chromatography or protein A-Sepharose column chromatography, etc.

The present inventors have established the anti-human BGP monoclonal antibody (MBG 04F5) and anti-bovine BGP monoclonal antibody (MBG 14AX) and examined their characteristics. As a result, it has been found that MBG 04F5 recognizes N-terminal to intermediate portion of human BGP since it strongly recognizes the human BGP (12 to 33) and does not react with N-terminal and C-terminal fragments. It has been also shown that MBG 14AX recognizes C-terminal side since it strongly recognizes the human BGP (30 to 49) and does not react with N-terminal to intermediate portion thereof.

As the immunological assay method of human BGP using the above monoclonal antibodies MBG 14AX and MBG 04F5, there may be mentioned RIA which is a second antibody method, the sandwich type EIA methods, the sandwich type fluorescent immuno-assay (FIA) method and the sandwich type IRMA method. With respect to the IRMA method, as shown in Reference examples, the one step IRMA method may be mentioned wherein a sample or a standard BGP, a predetermined amount of monoclonal antibody MBG 14AX which is radioactive isotope labelled, and polystyrene beads covered by monoclonal antibody MBG 04F5 are reacted, and then the dose of radioactivity bound to the beads is measured. During this time, the system wherein MBG 14AX is immobilized on polystyrene beads and MBG 04F5 is radioactive isotope labelled are also possible. Further, the so-called two step IRMA wherein a sample or a standard BGP is first reacted with antibody-covered beads, and then after removing the reaction solution, a monoclonal antibody which is radioactive isotope labelled is reacted thereto is also possible. Moreover, the reverse reaction IRMA wherein a sample or a standard BGP is first reacted with a monoclonal antibody which is isotope labelled, and then reacted with antibody-coated beads is also possible.

At this time, as the carrier to immobilize the antibody, there may be utilized a carrier for antigen-antibody which is used for general immunoassay such as particulates made of a glass, magnetic material or plastics, or spherical materials (beads), tube and plate. To these carriers was immobilized an antibody which recognizes N-terminal, intermediate portion or C-terminal of the human BGP physically or by the covalent bonding. The antibody to be used at this time may by either the monoclonal antibody or the polyclonal antibody since they can be treated in the same manner.

Radioactive isotope labelling of an antibody which recognizes N-terminal, intermediate portion or C-terminal of the human BGP can be carried out by incorporating an radioactive isotope such as $^{125}I$ by the known methods such as Chloramine-T method, lactoperoxidase method, Iodogen method and Bolton-Hunter method.

The RIA due to the second antibody method is possible either the momoclonal antibody or polyclonal antibody. The method may include two methods one of which is a competitive method wherein a sample or a standard BGP, an anti-BGP antibody and a human BGP which is radioactive isotope labelled are simultaneously reacted, B/F separation is carried out by a second antibody and measuring a dose of radioactivity bound to the antibody, and the other is a non-equilibrium method wherein addition of a human BGP which is radioactive isotope labelled is delayed for several hours to 1 day.

The sandwich EIA and the sandwich FIA are basically the same as the IRMA but different therefrom in using an enzyme label or a fluorescent substance label in place of an isotope label.

An antibody for labelling may be used by purifying until IgG and it is used as a labelling substance as it were, or used by digesting with pepsin to F(ab')$_2$ or reducing with 2-mercaptoethanol to Fab'.

As the enzyme for labelling, alkaline phosphatase, β-D-galactosidase, peroxidase and glucose oxidase can be used.

As the fluorescent labelling, a fluorescent substance such as fluorescein, fluorescein isocyanate, fluorescein isothiocyanate and rhodamine may be used; and it is also possible to use a method in which an europium ion is used as a label.

In the one step IRMA shown in Reference example, it has been shown that only the intact BGP (1 to 49) is measured so that the problem of specificity in the conventional RIA can be overcome. Therefore, it is suggested that it is a measuring system capable of providing available data for clinically evaluating bone metabolism.

EXAMPLES

The present invention is described in detail below by referring to Examples, but the present invention is not limited by these Examples at all.

EXAMPLE 1

Synthesis of γ-carboxyglutamic acid derivative

Step a

SYNTHESIS OF COMPOUND (V)

Into 200 ml of an acetone solution of 25 g of N-t-butyloxycarbonylserine (IV) were added 26.8 g of benzylbromide and 16.9 g of triethylamine, and the mixture was heated under reflux with stirring for 2 days. After completion of the reaction, the reaction mixture was concentrated under reduced pressure to evaporate the solvent, and water and diethyl ether were added to the residue, followed by thorough shaking and liquid separation. The ether was washed twice with water, subsequently once with saturated aqueous sodium chloride. The ether layer was separated, dried and then ether was evaporated under reduced pressure to give 30.3 g of an oily compound (V) (yield 97.8%).

Step b

SYNTHESIS OF COMPOUND (VI)

Into a solution of 31 g of the compound (V) obtained in the step a dissolved in 100 ml of pyridine was added 23 g of p-toluenesulfonyl chloride, and after stirring at 0° C. for 3 hours, 2.3 g of p-toluenesulfonyl chloride was further added, followed further by stirring for 4 hours. After completion of the reaction, the reaction mixture was poured into ice-water, the mixture was stirred, and the white crystals formed were collected by filtration to give 37.4 g of the compound (VI) (yield: 79.3%).

Step c

SYNTHESIS OF COMPOUND (VII)

Into a solution of 37.4 g of the compound (VI) obtained in the step b dissolved in 200 ml of a mixed solution of ethyl acetate/diethyl ether (1:1) was gradually added dropwise 17.2 ml of diethylamine. and the mixture was stirred at room temperature for 3 hours. After completion of the reaction, the reaction mixture was cooled to 0° C., filtered and the filtrate was subjected to evaporation under reduced pressure to give 23.0 g of an oily compound (VII) (yield: 99.3%).

Step d

SYNTHESIS OF COMPOUND (IX)

Into 250 ml of a toluene solution of 33 g of dimethyl malonate (VIII) were added 75 g of cyclohexanol and 1.25 g of p-toluenesulfonic acid monohydrate, and the mixture was heated under reflux with stirring for 42 hours. After completion of the reaction, the reaction mixture was washed twice with an aqueous sodium hydrogen carbonate, twice with water, and further twice with saturated aqueous sodium chloride. The organic layer was dried over anhydrous sodium sulfate, and the solvent was evaporated under reduced pressure. The residue was distilled, and the distillates at 128° to 130° C. were collected by separation to give 49.7 g of an oily compound (IX) (yield: 74.2%).

Step e

SYNTHESIS OF COMPOUND (X)

Into 150 ml of a THF suspension of 3.32 g of 60% sodium hydride in mineral oil was gradually added dropwise a solution of 22.8 g of the compound (IX) obtained in the step d dissolved in THF under cooling to 5° C. After foaming ceased, the mixture was stirred at room temperature for one hour. Next, a solution of 23 g of the compound (VII) obtained in the step c dissolved in THF was added dropwise into the previous reaction mixture under ice-cooling, and the mixture was stirred for one hour. After completion of the reaction, the reaction mixture was mixed with 0.1 N citric acid under ice-cooling and the mixture extracted with diethyl ether. The ether layer was washed with water, then with saturated aqueous sodium chloride, and after drying, the solvent was evaporated under reduced pressure. To the residue were added acetonitrile and n-hexane to effect extraction, and the acetonitrile layer was separated, followed by evaporation of the solvent under reduced pressure. The residue was purified by silica gel column chromatography with diethyl ether/n-hexane (2:5) to give 32.7 g of an oily compound (X) (yield: 72.5%).

Step f

SYNTHESIS OF COMPOUND (XI)

Into a solution of 28.8 g of the compound (X) obtained in the step e dissolved in 300 ml of ethanol was added 1.5 g of 5% palladium-carbon, and the mixture was stirred in hydrogen gas atmosphere at room temperature for 3 hours. After completion of the reaction, the catalyst was removed and ethanol was evaporated under reduced pressure to give 23.0 g of an oily compound (XI) (yield: 95.7%).

$F_{ab}$ mass analysis $[M+H]^+$ Found: 456, Calcd.: 456.

Step g

OPTICAL RESOLUTION OF COMPOUND (XI)

The compound (XI) obtained in the step f (23.0 g) was dissolved in 100 ml of ethyl acetate, 200 ml of an ethyl acetate solution of 17.1 g of quinine was added to the solution and the mixture was shaken and then left to stand at room temperature for 3 days. The crystals formed were collected by filtration to obtain 21.8 g of an L-γ-carboxyglutamic acid derivative quinine salt with an optical purity of 39.2% as white needles (yield: 53.0%). This was further recrystallized three times repeatedly with methanol, followed by suspending in ethyl acetate and desalting with 1 N citric acid. The organic layer was washed with saturated aqueous sodium chloride, dried, and then ethyl acetate was evaporated under reduced pressure. To the residue was added n-hexane, and white crystals formed were collected by filtration to give 4.79 g of an L-γ-carboxyglutamic acid derivative (II) with an optical purity of 97.2% (yield: 20.6%).

Figure 2:
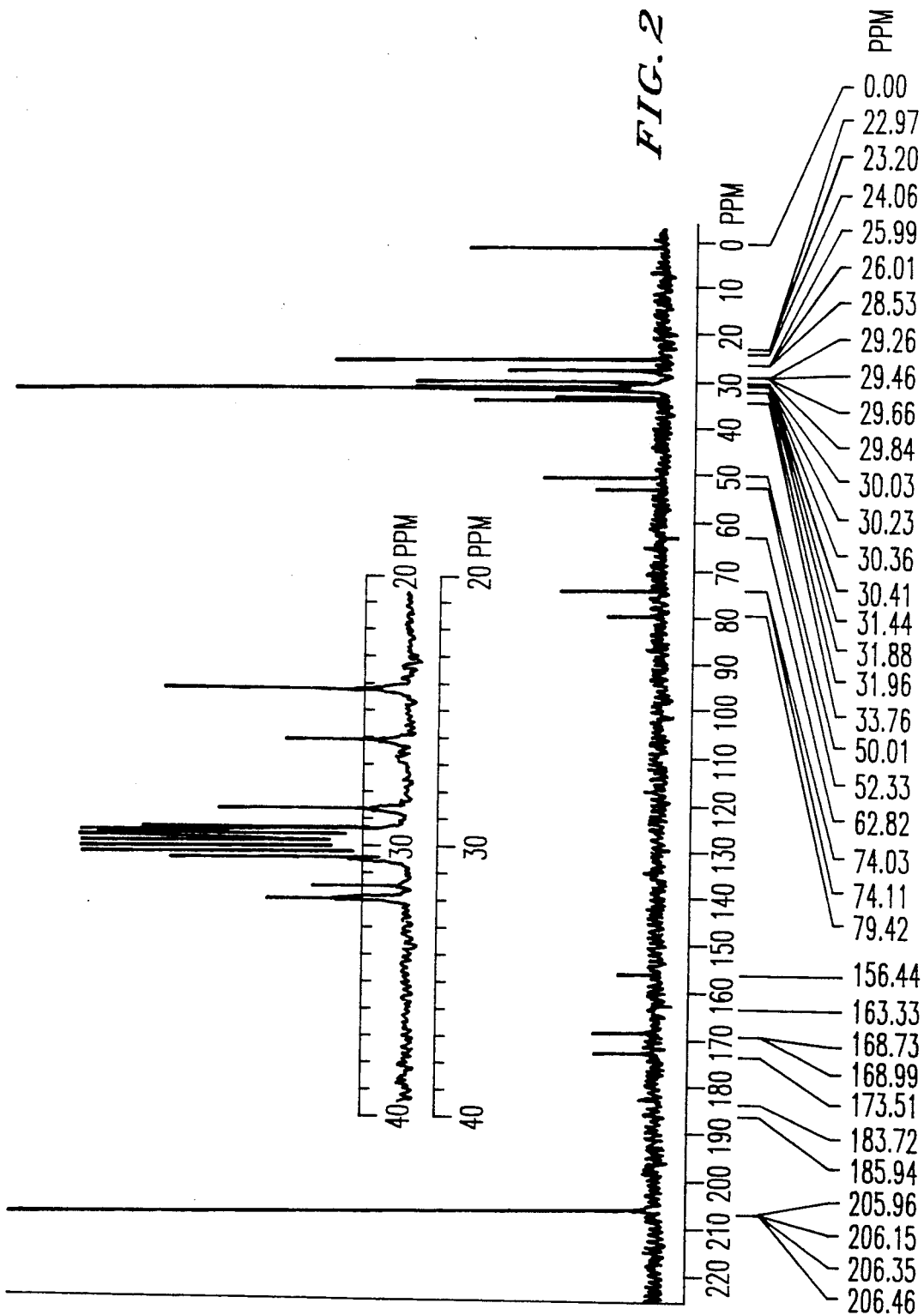
FIG. 2 is a chart showing its $^{13}$C-NMR spectrum.
Figure 3:
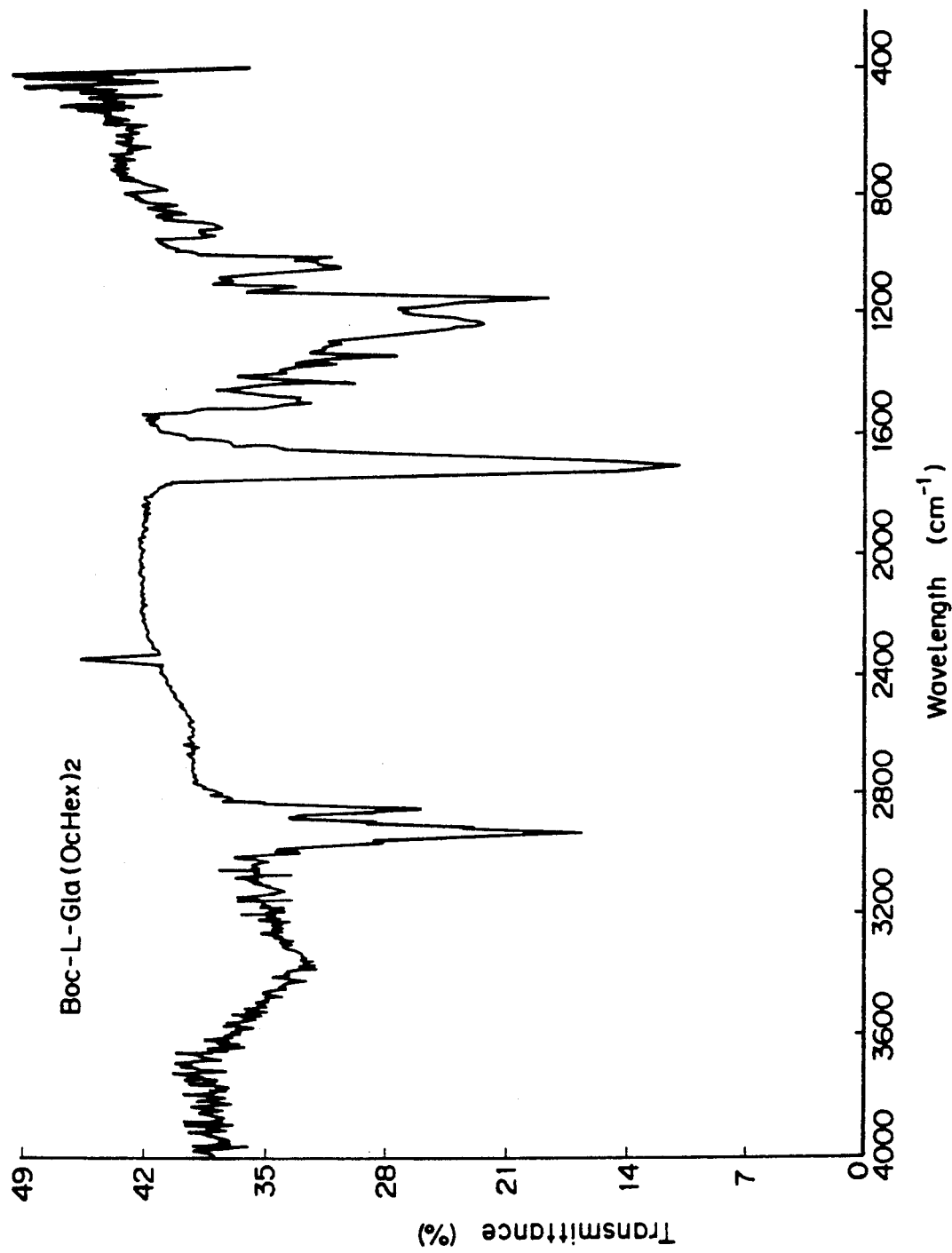
FIG. 3 is a chart showing its IR-absorption spectrum.

Nuclear magnetic resonance spectra of the optically active isomers (II) obtained are shown in FIG. 1 and FIG. 2, and the IR-absorption spectrum in FIG. 3.

Elemental analysis (as $C_{23}H_{37}NO_8$)

|   | C | H | N |
| --- | --- | --- | --- |
| Found: | 60.70 | 8.42 | 3.00 |
| Calcd.: | 60.64 | 8.19 | 3.08 |

$F_{ab}$ mass analysis $[M+H]^+$ Found: 456, Calcd.: 456.
Optical rotation $[\alpha]_D$: −4.9 ° (C 1.05, methanol).

EXPERIMENTAL EXAMPLE 1

OPTICAL PURITY ASSAYING METHOD

The quinine salt of the optically active isomer (II) obtained in the above Example 1 (46.8 mg) was suspended in ethyl acetate and desalted with 1 N citric acid. The organic layer was washed with saturated aqueous sodium chloride and dried. Evaporation of ethyl acetate under reduced pressure gave 27.5 mg of a free γ-carboxyglutamic acid derivative (hereinafter called sample (a)). Its whole amount was dissolved in 2.8 ml of dichloromethane and to the resultant solution were added 14.2 mg of 2-chloro-1-methylpyridinium, 8.2 μl of R-(+)-1-(α-naphthyl)ethylamine and 26.6 μl of n-butylamine, and the reaction was carried out at 40° C. for 2 hours. After completion of the reaction, diastereomer fractions formed by thin layer chromatography were separated. The fractions were eluted with ethyl acetate, and then the residue obtained by evaporation under reduced pressure was analyzed by high performance liquid chromatography under the following conditions.

ANALYTICAL CONDITIONS

Column: Ricrosolve Si60, 5 μm φ4.6×250 mm (Merck).
Moving phase: ethyl acetate/n-hexane = 1 : 3.
Flow rate: 1 ml/min.
Detection: UV 254 nm.
Column temperature: 30° C.
Data processing device: Chromatopack C-R3A (Shimazu Seisakusho).

Also for 11.2 mg of the racemic mixture (XI) of the above compound, diastereomers with 3.3 μl of R-(+)-1-(α-naphthyl)ethylamine were similarly synthesized, and analyzed by high performance liquid chromatography under the same conditions as mentioned above. The results are shown in the following Table.

| Diastereomer | Peak area | |
| acyl components | L*1 | D*1 |
| --- | --- | --- |
| Sample (a) | 284,147 | 4,396 |
| Racemic mixture | 207,611 | 222,716 |

*1(Configuration of diastereomer acyl component side chain. Determined by Experimental example 2.)

The optical purity was determined by the following formula.

Optical purity (%) = (2x − 1) × 100, wherein $$X = \frac{L \text{ area of sample (a)}}{\left(\begin{array}{c} L \text{ area} \\ \text{of} \\ \text{sample} \\ \text{(a)} \end{array}\right) + \left(\left(\begin{array}{c} D \text{ area} \\ \text{of} \\ \text{sample} \\ \text{(a)} \end{array}\right) \times \left(\frac{L \text{ area of racemic mixture}}{D \text{ area of racemic mixture}}\right)\right)}$$

The optical purity of the above optically active isomer (L isomer) (II) was found to be 97.2%.

EXPERIMENTAL EXAMPLE 2

DETERMINATION OF OPTICAL ISOMERS

One mg of the above optically active isomer (II) was hydrolyzed with 0.1% phenol containing 6 N hydrochloric acid under reduced pressure at 110° C. for 22 hours. After completion of the reaction, hydrochloric acid was volatilized and the residue was dissolved in 5 ml of 0.1 N hydrochloric acid. To 30 μl of the solution were added 30 μl of 50 mg/ml of triethylamine acetonitrile solution and 60 μl of 10 mg/ml of GITC acetonitrile solution, and the reaction was carried out at room temperature for 20 minutes. The same procedures were conducted also for 1 mg of the standard L-glutamic acid and D-glutamic acid and blank. The respective solutions obtained were analyzed by reverse phase HPLC.

ANALYTICAL CONDITIONS

Column: YMC-R, 5 μm φ4.6×250 mm (Yamamura Kagaku).
Moving phase: A - 0.1% phosphoric acid, B - acetonitrile.
Concentration gradient: A/B = 100/10→50/50, eluted according to a linear concentration gradient for 30 minutes.
Detection: UV 250 nm.
Column temperature: room temperature.
Data processing device: Chromatopack C-R3A (Shimazu Seisakusho).

Analysis was conducted in the order of L-glutamic acid reaction mixture, D-glutamic acid reaction mixture, optically active isomer (II) reaction mixture, D-glutamic acid reaction mixture + optically active isomer (II) reaction mixture and blank. The relative retention times of the diastereomers formed on the chromatogram were L-glutamic acid diastereomer < D-glutamic acid diastereomer, and the optically active diastereomer was found to be enriched in L-glutamic acid.

From the above results, the optically active isomer (II) was identified to be the L-isomer.

EXAMPLE 2

SYNTHESIS OF GLA[17] HUMAN OSTEOCALCIN REPRESENTED BY THE FORMULA

```
 1                    5                       10
Tyr—Leu—Tyr—Gln—Trp—Leu—Gly—Ala—Pro—Val—Pro—

15                   20
Tyr—Pro—Asp—Pro—Leu—Gla—Pro—Arg—Arg—Gla—Val—

25                           30
Cys—Gla—Leu—Asn—Pro—Asp—Cys—Asp—Glu—Leu—Ala—

35                  40
Asp—His—Ile—Gly—Phe—Gln—Glu—Ala—Tyr—Arg—Arg—

45              49
Phe—Tyr—Gly—Pro—Val
```

(with a bracket connecting position 25 to position 30 above Cys...Cys)

(1) INTRODUCTION OF 48-POSITION PRO INTO BOC-VAL-PAM RESIN

1) DEPROTECTION AND NEUTRALIZATION

An amount 0.746 g of Boc-Val-Pam resin (0.67 mmole/g) was washed twice with DCM. To the resin was added 8 ml of a 33 % TFA solution (solvent: DCM), and after stirring for 80 seconds, the mixture was filtered. Further, 80 ml of a 50 % TFA solution (solvent: DCM) was added, and after stirring for 18.5 minutes, the mixture was subjected to filtration to eliminate Boc groups. The resin obtained was consecutively treated with the solvents shown below, and filtration effected after each treatment.

DCM (×3, each for 30 seconds).
10% DIEA/DMF (×2, each for one minute).
DMF (×5, each for 30 seconds).

2) PREPARATION OF BOC-PRO SYMMETRIC ACID ANHYDRIDE

After 2 mmole of Boc-Pro was dissolved in 3 ml of DCM, 2 ml of a 0.5 M DCC solution (solvent: DCM) was added thereto to carry out the reaction for 8 minutes, thereby forming symmetric acid anhydride. After removal of dicyclohexylurea by-produced by filtration, 4 ml of DMF was added, followed subsequently by evaporation of DCM in the reaction mixture.

3) CONDENSATION REACTION

The DMF solution of the Boc-Pro symmetric acid anhydride prepared in 2) was added to the Val-Pam resin prepared in 1) and the reaction was carried out at room temperature for 18 minutes. After completion of the reaction, the reaction mixture was washed with DCM for 5 times.

(2) INTRODUCTION OF THE RESPECTIVE AMINO ACIDS AT 47- TO 1-POSITIONS

Similarly as described in (1), Boc-Pro-Val-Pam resin was successively coupled with the protective amino acids corresponding to the respective constituent amino acids from the 47-position to the 1-position of Gla$^{17}$ human osteocalcin. Table 1 shows the protected amino acids, synthetic methods, etc. used in the respective reaction steps.

In the Table, concerning the synthetic cycle, the method (1), the method (2), the method (3) mean deprotection, neutralization and condensation reactions carried out according to the following procedures, respectively.

Method (1)

1) Deprotection with 33% TFA (solvent: DCM) for 80 seconds;
2) Deprotection with 50% TFA (solvent: DCM) for 18.5 minutes;
3) DCM washing, ×3, each for 30 seconds;
4) Neutralization with 10% DIEA/DMF, ×2, each for 1 minute;
5) DMF washing, ×5, each for 30 seconds;
6) Condensation reaction for 18 minutes;
7) DCM washing, ×5, each for 30 seconds.

Method (2)

1)–5): the same as in Method (1);
6) Condensation reaction for 26 minutes;
7) the same as in Method (1).

Method (3)

1)–5): the same as in Method (1);
6) Condensation reaction for 42 minutes;
7) DMF washing, ×3, each for 30 seconds;
8) Neutralization with 10% DIEA/DMF for 45 seconds;
9) DMF washing for 30 seconds;
10) DCM washing for 3 times, each for 30 seconds;
11) Condensation reaction for 42 minutes;
12) DMF washing for 30 seconds;
13) DCM washing, ×5, each for 30 seconds.

Also, in the Table, concerning synthesis of symmetric acid anhydride or HOBt ester, Method (1), Method (2), Method (3), Method (4) and Method (5) mean syntheses of symmetric acid anhydride or HOBt ester according to the following procedures, respectively.

Method (1)

After 2 mmole of Boc-amino acid was dissolved in 3 ml of DCM, 2 ml of 0.5 M DCC solution (solvent DCM) was added thereto, the reaction was carried out for 8 minutes to form a symmetric acid anhydride. After removal of dicyclohexylurea by-produced by filtration, 4 ml of DMF was added, and subsequently DCM in the reaction mixture was evaporated.

Method (2)

After 2 mmole of Boc-amino acid was dissolved in 3 ml of DCM, 2 ml of 0.5 M DCC solution (solvent: DCM) was added thereto, and the reaction was carried out for 8 minutes to form a symmetric acid anhydride. After removal of dicyclohexylurea by-produced by filtration, 1 ml of DMF was added and the DCM in the reaction mixture was evaporated.

Method (3)

After 2 mmole of Boc-amino acid was dissolved in 0.3 ml of DMF and 2.5 ml of DCM, 2 ml of 0.5 M DCC solution (solvent: DCM) was added thereto, and the reaction was carried out for 8 minutes to form a symmetric acid anhydride. After dicyclohexylurea by-produced was removed by filtration, 4 ml of DMF was added and subsequently DCM in the reaction mixture was evaporated.

Method (4)

After 4 ml of 0.5 M HOBt and 0.3 ml of DCM were added into 2 mmole of Boc-amino acid to be dissolved therein, 4 ml of 0.5 M DCC solution (solvent: DCM) was added to the solution, and the reaction was carried out for 33 minutes to form an HOBt ester. After dicyclohexylurea by-produced was removed by filtration, 3 ml of DCM in the reaction was evaporated. Preparation of the HOBt ester according to this operation were practiced twice for one residue.

Method (5)

After 4 ml of 0.5 M HOBt and 1.5 ml of DCM were added to 2 mmole of Boc-amino acid to be dissolved therein, 4 ml of 0.5 M DCC solution (solvent: DCM) was added to the solution, and the reaction was carried out to form an HOBt ester. After removal of dicyclohexylurea by-produced by filtration, 3 ml of DCM in the reaction mixture was evaporated. Preparation of the HOBt ester according to this operation was performed twice for one residue.

After introduction of the amino acid at the 1-position, 20 ml of a 33% TFA solution (solvent: DCM) was added to the resin peptide, and the mixture was stirred for 80 seconds and then filtered. Further, 20 ml of a 50% TFA solution (solvent: DCM) was added, and the mixture was stirred for 18.5 minutes and filtered to eliminate Boc groups. The resin obtained was successively treated with the following solvents, and filtered after each treatment:

DCM (×3, each for 30 seconds);
10% DIEA/DCM (×2, each for one minute);
DCM (×5, each for 30 seconds).

Next, the present resin peptide was dried under reduced pressure for one day and night to obtain a dry resin peptide.

TABLE 1

| Position of amino acid | Protected amino acid | Synthesis cycle | Synthesis of symmetric acid anhydride or HOBt ester | Coupling number |
|---|---|---|---|---|
| 47 | Bos—Gly | Method (1) | Method (2) | 1 |
| 46 | Bos—Tyr(Br—Z) | Method (1) | Method (1) | 1 |
| 45 | Bos—Phe | Method (2) | Method (1) | 1 |
| 44 | Bos—Arg(Tos) | Method (3) | Method (5) | 2 |
| 43 | Bos—Arg(Tos) | Method (3) | Method (5) | 2 |
| 42 | Bos—Tyr(Br—Z) | Method (1) | Method (1) | 1 |
| 41 | Bos—Ala | Method (1) | Method (1) | 1 |
| 40 | Bos—Glu(OBzl) | Method (1) | Method (1) | 1 |
| 39 | Bos—Gln | Method (3) | Method (4) | 2 |
| 38 | Bos—Phe | Method (2) | Method (1) | 1 |
| 37 | Bos—Gly | Method (1) | Method (2) | 1 |
| 36 | Bos—Ile | Method (2) | Method (1) | 1 |
| 35 | Bos—His(Tos) | Method (2) | Method (2) | 1 |
| 34 | Bos—Asp(OBzl) | Method (1) | Method (1) | 1 |
| 33 | Bos—Ala | Method (1) | Method (1) | 1 |
| 32 | Bos—Leu | Method (2) | Method (3) | 1 |
| 31 | Bos—Glu(OBzl) | Method (1) | Method (1) | 1 |
| 30 | Bos—Asp(OBzl) | Method (1) | Method (1) | 1 |
| 29 | Bos—Cys(4CH$_3$Bzl) | Method (2) | Method (1) | 1 |
| 28 | Bos—Asp(OBzl) | Method (1) | Method (1) | 1 |
| 27 | Bos—Pro | Method (2) | Method (1) | 1 |
| 26 | Bos—Asn | Method (3) | Method (4) | 2 |
| 25 | Bos—Leu | Method (2) | Method (3) | 1 |
| 24 | Bos—Gla(OcHex)$_2$ | Method (1) | Method (1) | 1 |
| 23 | Bos—Cys(4CH$_3$Bzl) | Method (2) | Method (1) | 1 |
| 22 | Bos—Val | Method (2) | Method (1) | 1 |
| 21 | Bos—Gly | Method (1) | Method (1) | 1 |
| 20 | Bos—Gly | Method (3) | Method (5) | 2 |
| 19 | Bos—Arg(Tos) | Method (3) | Method (5) | 2 |
| 18 | Bos—Pro | Method (2) | Method (1) | 1 |
| 17 | Bos—Gla(OcHex)$_2$ | Method (1) | Method (1) | 1 |
| 16 | Bos—Leu | Method (2) | Method (3) | 1 |
| 15 | Bos—Pro | Method (2) | Method (1) | 1 |
| 14 | Bos—Asp(OBzl) | Method (1) | Method (1) | 1 |
| 13 | Bos—Pro | Method (2) | Method (1) | 1 |
| 12 | Bos—Tyr(Br—Z) | Method (2) | Method (1) | 1 |
| 11 | Bos—Pro | Method (2) | Method (1) | 1 |
| 10 | Bos—Val | Method (1) | Method (1) | 1 |
| 9 | Bos—Pro | Method (1) | Method (1) | 1 |
| 8 | Bos—Ala | Method (1) | Method (1) | 1 |
| 7 | Bos—Gly | Method (1) | Method (2) | 1 |
| 6 | Bos—Leu | Method (2) | Method (3) | 1 |
| 5 | Bos—Trp | Method (2) | Method (3) | 1 |
| 4 | Bos—Gln | Method (3) | Method (4) | 2 |
| 3 | Bos—Tyr(Br—Z) | Method (1) | Method (1) | 1 |
| 2 | Bos—Leu | Method (2) | Method (3) | 1 |
| 1 | Bos—Tyr(Br—Z) | Method (1) | Method (1) | 1 |

(3) Decomposition with HF

A part (815 mg) of the dried resin peptide was weighed, placed in a reactor (made of Teflon) for HF decomposition, 2 ml of anisole was added, and the mixture was left to stand overnight to swell the resin. The above reactor was a stirrer introduced therein was mounted on a HF decomposition device (Peptide Research Institute), placed in a dry ice-methanol bath, and 18 ml of HF was introduced into the reactor. The mixture was stirred in an ice bath at 0° C. for one hour. HF was gradually evaporated under reduced pressure. After 3 hours, the reactor was dismantled and the resin peptide decomposed product was taken out from the reactor by use of anhydrous diethylether and washed with anhydrous diethylether. The resin peptide decomposed product was added into 50 ml of 30% acetic acid to dissolve the deprotected peptide. This was previously substituted to acetic acid form for the purpose of salt exchange and passed through a Dowex 1×2 ion exchange resin column. To the fractions passed as such were added water to adjust the acetic acid concentration to 1 N, followed by lyophilization to obtain 475 mg of reduced type crude Gla$^{17}$ human osteocalcin.

(4) FORMATION OF DISULFIDE BOND BY AIR OXIDATION

Of the reduced type crude human osteocalcin obtained in (3), 287 mg was dissolved in 0.1 M ammonium acetate solution (pH 8.5) and 100 equivalents of DTT were added, followed by reduction at 40° C. for 5 hours. By this reduction operation, the dimer which can be formed by oxidation of mercapto group is returned to the monomer.

The reaction mixture was adjusted to pH 4.0 by addition of acetic acid and then centrifuged. After removal of the supernatant, the precipitates were redissolved by addition of 30% acetic acid. Subsequently, DTT and salts were removed by gel chromatography by use of Sephadex G25 (Pharmacia). Next, the fractions containing the reduced type crude Gla$^{17}$ human osteocalcin were gradually added dropwise into 0.1 M ammonium acetate solution (pH 7.5) while maintaining pH constant. The peptide concentration at this time was made about $1.5 \times 10^{-6}$ M. After formation of disulfide bond by stirring at room temperature for 15 days, the reaction mixture was adsorbed onto a column filled with octadecylsilica (ODS column, $\phi 2 \times 30$ cm), washed with 0.1% TFA, and then the peptide was eluted with 60% acetonitrile solution. After evaporation of acetonitrile under reduced pressure, the residue was lyophilized to obtain crude Gla$^{17}$ human osteocalcin. The disulfide formation reaction was monitored by the known Elman test by use of 5,5'-dithiobis(2-nitrobenzoic acid), and the reaction product finally obtained had an oxidation ratio of 95%.

(5) PURIFICATION OF GLA$^{17}$ HUMAN OSTEOCALCIN BY REVERSE PHASE HPLC

The crude Gla$^{17}$ human osteocalcin obtained in (4) was dissolved in 30% acetic acid (10 mg/ml) and purified by high performance liquid chromatography isocratic elution. The column employed was YMC-D (YMC, $\phi 2 \times 30$ cm), and the eluants employed were A solution of water (100) - 10% TFA (1) and B solution of water (40) - acetonitrile (60) - 10% TFA (1), and elution was carried out under the conditions of A (48) - B (52). Here, the numerals within the brackets are volume ratios. The fractions corresponding to Gla$^{17}$ human osteocalcin were separated and lyophilized to give white powder.

Further, the above white powder was dissolved in 30% acetic acid (10 mg/ml), and repurified similarly as described above. As the eluant, A/B=51/49 was employed. The fractions corresponding to Gla$^{17}$ human osteocalcin were separated and lyophilized to give white powder.

The white powder obtained by repurification was further dissolved in 30% acetic acid (10 mg/ml), and purification was further carried out under the same conditions as in repurification. Fractions corresponding to Gla$^{17}$ human osteocalcin were collected and lyophilized to obtain white powder. This product was dissolved in 30% acetic acid, desalted by Sephadex G25 column chromatography, then water was added to the Gla$^{17}$ human osteocalcin fractions to control the acetic acid concentration to 1 N, followed by lyophilization, to give 6.6 mg of the desired Gla$^{17}$ human osteocalcin.

(6) STRUCTURE IDENTIFICATION AND PURITY ASSAY OF PURIFIED GLA$^{17}$ HUMAN OSTEOCALCIN

Analytical values of amino acids of the purified Gla$^{17}$ human osteocalcin are shown in Table 2.

This product (100 μg) was dissolved in 1% NH$_4$HCO$_3$, and digested at 25° C. for 2 hours with addition of 1/10 equivalent of trypsin-TPCK (Worsinton). As the result of measurement of the digested product by reverse phase HPLC under the following measuring conditions (1), three main peaks were recognized at 18.9 min., 47.6 min and 66.8 min. on the chromatogram, and from the results of amino acid analysis and Fab mass analysis, they were found to be the peptides corresponding to the 45-49 positions, 20-43 position and 1-19 positions of Gla$^{17}$ human osteocalcin, respectively.

TABLE 2

Amino acid composition of purified Gla$^{17}$ human osteocalcin

| Amino acid | Molar ratio | Amino acid number |
|---|---|---|
| Gla* | 2.93 | 3 |
| Asx** | 5.23 | 5 |
| Glx*** | 4.11 | 4 |
| Gly | 3.30 | 3 |
| Ala | 3.19 | 3 |
| Cys**** | 1.86 | 2 |
| Val | 2.93 | 3 |
| Ile | 1.00 | 1 |
| Leu | 5.52 | 5 |
| Tyr | 5.63 | 5 |
| Phe | 2.29 | 2 |
| His | 1.02 | 1 |
| Arg | 4.54 | 4 |
| Pro | 6.96 | 7 |
| Trp* | 0.93 | 1 |

*hydrolyzed with 2.5 N NaOH, 110° C., 22 hours
**Asn and Asp
***Gln and Glu hydrolyzed with 2.5 N NaOH, 110° C., 22 hours
****quantitated as S-carboxymethylcysteine

MEASURING CONDITIONS (1)

Column: YMC-R (φ4.6×250 mm)
Flow rate: 1 ml/min.
Eluent: A solution (water:acetonitrile:10% TFA=100 : 0:1), B solution (water:acetonitrile:10% TFA =40 : 60 : 1).
Concentration gradient: A/B=80/20 (0 min)→45/55 (70 min)→0/100 (70 min)→0/100 (73 min).
Measurement wavelength: 220 nm.

On the other hand, the purified Gla$^{17}$ human osteocalcin was subjected to purity assay by reverse phase HPLC under the measuring conditions (2) shown below.

MEASURING CONDITIONS (2)

Column: YMC-R (φ4.6×250 mm)
Flow rate: 1 ml/min.
Eluent: A solution (water:acetonitrile:10% TFA=100 : 0:1), B solution (water:acetonitrile:10% TFA =40 : 60 : 1).
Concentration gradient: A/B=100/0 (0 min)→100/0 (5 min)→0/100 (35 min)→0/100 (40 min).
Measurement wavelength: 220 nm.

As the result, a single strong absorption was recognized based on the peptide at a retention time of 30.7 min., and this was Gla$^{17}$ human osteocalcin of the present invention.

EXAMPLE 3

Synthesis of Glu$^{17}$ human osteocalcin represented by the formula

```
 1                      5                    10
Tyr—Leu—Tyr—Gln—Trp—Leu—Gly—Ala—Pro—Val—Pro—

15                   20
Tyr—Pro—Asp—Pro—Leu—Glu—Pro—Arg—Arg—Gla—

25                          30
Val—Cys—Gla—Leu—Asn—Pro—Asp—Cys—Asp—Glu—Leu—

35                40
Ala—Asp—His—Ile—Gly—Phe—Gln—Glu—Ala—Tyr—Arg—

45              49
Arg—Phe—Tyr—Gly—Pro—Val
```

The solid phase synthesis was carried out under the same conditions as in Example 2 except for using Boc-Glu(OBzl) in place of using Boc-Gla(OcHex)$_2$ in introduction of the amino acid at the 17-position to obtain a protected peptide resin. A part (500 mg) of the protected resin was HF decomposed in the same manner as in Example 2. The reduced type crude Glu$^{17}$ human osteocalcin obtained was oxidized, purified in the same manner as in Example 2 to give 3.2 mg of Glu$^{17}$ human osteocalcin.

According to the method of the present invention, introduction of Gla can be introduced more easily in Gla$^{17}$ human osteocalcin and Glu$^{17}$ human osteocalcin, whereby chemical synthesis is rendered possible.

REFERENCE EXAMPLE

PRODUCTION OF HUMAN BGP MEASURING TEST KIT USING HUMAN BGP

(a) PRODUCTION OF ANTI-BOVINE BGP MONOCLONAL ANTIBODY

After preparing a bound product of a bovine BGP extracted from bone of bovine and purified to a purity of 95% or higher and a swine thyroglobulin, an emulsion was prepared with a Freund's complete adjuvant and immunized to mouse (Balb/c species). After confirming appearance of antibody to bovine BGP in blood of mouse, cell suspension was prepared by using delivered spleen. Then, 1 to 5×10$^8$ spleen cells were fused with 2 to 10×10$^7$ mouse myeloma cells (P3-X63-Ag8-U1) under the conditions described in a literature (Galfre C, Milstein C., Methods Enzymol. 1981; 73: 3-46). Hybridomas were cultivated in a Dulbecco's modified-Eagle's medium containing 10% of bovine fetal serum and generation of anti-bovine BGP antibody was examined. Antibody forming hybridomas were cultivated to examine generation of anti-bovine BGP antibody. Cloning of antibody forming hybridoma was repeated twice or more to obtain clones. By the method of inoculating cultivated hybridomas to abdominal cavity of mouse (Balb/c species) and obtaining ascites after 2 weeks, a large amount of monoclonal antibody was obtained.

2. PRODUCTION OF ANTI-HUMAN BGP MONOCLONAL ANTIBODY

After preparing a bound product of Gla$^{17}$ human osteocalcin with a purity of 95% or more obtained by chemically synthesizing and purifying according to the method of Example 2 and a swine thyroglobulin, hybridoma was obtained in the same producing method of anti-bovine BGP monoclonal antibody according to the above 1, and a large amount of anti-human BGP monoclonal antibody was obtained according to the ascites method.

3. PREPARATION OF POLYSTYRENE BEADS COVERED BY ANTI-HUMAN BGP MONOCLONAL ANTIBODY

Beads made of polystyrene (diameter: 6.3 mm) were dipped in a mouse ascites purified IgG fraction solution of anti-human BGP monoclonal antibody prepared with a concentration of 16 μg/ml by using 0.3 ml of 0.1 mole bicarbonate buffer (pH 9.6) per one bead, and allowed to stand at room temperature overnight. Thereafter, the beads were washed with a phosphate buffer containing 0.1% Tween 20 (trade name) and then dried in vacuum.

4. PRODUCTION OF ANTI-BOVINE BGP MONOCLONAL ANTIBODY LABELLED WITH $^{125}$I (IODINE)

According to a literature [Greenwood FC, Hunter WM, Glover JS., Biochem. J, 1963; 89: 114–123], IgG fraction of the anti-bovine BGP monoclonal antibody obtained from mouse ascites was labelled with $^{125}$I by the Chloramine T method.

5. DETERMINATION OF HUMAN BGP

Figure 4:
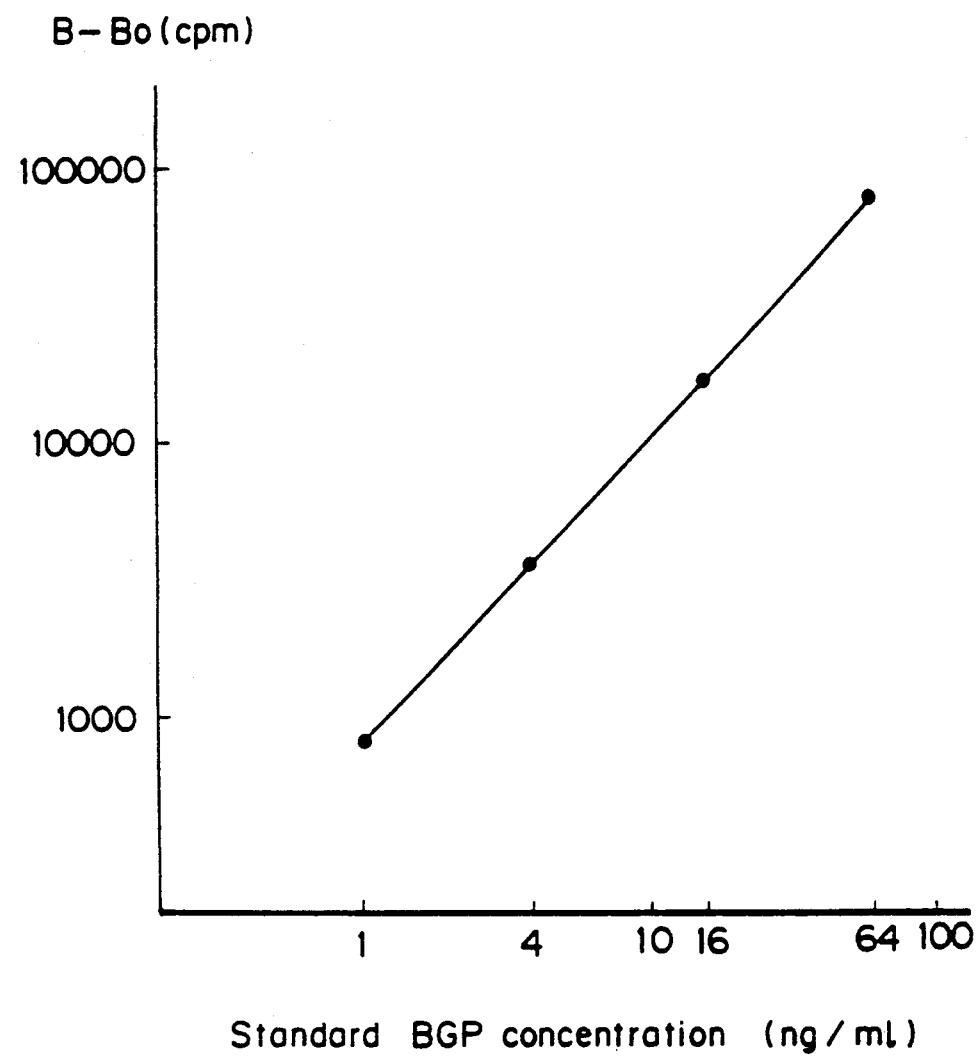
FIG. 4 is a BGP standard curve prepared based on the measured results shown in Table 3.

According to the so-called sandwich type radioactive immunoassay method wherein the measurement was carried out by covering a solid substrate with a monoclonal antibody A and labelling a monoclonal antibody B with $^{125}$I, determination of the human BGP was practiced. That is, in a plastic test tube, a 25 μl solution containing various concentration of human BGPs was placed and then 200 μl of $^{125}$I labelled anti-bovine BGP monoclonal antibody was placed, and further one polystyrene bead covered by the anti-human BGP monoclonal antibody was placed therein, it was shaked at room temperature for 3 hours, respectively. Next, after the reaction mixture was subjected to suction removal, the bead was washed with 2 ml of purified water three times. A dose of radioactivity of $^{125}$I labelled anti-bovine BGP antibody bound to the bead was measured by Well type gamma counter. The results are shown in Table 3. Finally, a dose of radioactivity (cpm) against logarithm of a human BGP concentration of a solution placed in a test tube was plotted against logarithm to prepare a dose-dependent curve. The resulting curve is shown in FIG. 4. If an unknown sample is measured in the same manner, a concentration thereof can be known from the dose-dependent curve. BGP concentrations of 66 normal sera were measured, and results ranging from 3.1 ng/ml (Mean - 2SD) to 12.7 ng/ml (Mean+2SD) with an average of 6.2 ng/ml were obtained.

TABLE 3

| Test tube No. | Content of test tube | Count (cpm) Found | Count (cpm) Average | B-Bo (cpm) Found | B-Bo (cpm) Average | BGP concentration (ng/ml) |
|---|---|---|---|---|---|---|
| 1 | Total count | 179630 | 179262 | | | |
| 2 | Total count | 178894 | | | | |
| 3 | Standard BGP 0 ng/ml | 573 | 562 | | | |
| 4 | Standard BGP 0 ng/ml | 551 | | | | |
| 5 | Standard BGP 1 ng/ml | 1495 | 1559 | 993 | 997 | |
| 6 | Standard BGP 1 ng/ml | 1662 | | 1060 | | |
| 7 | Standard BGP 4 ng/ml | 4689 | 4830 | 4127 | 4268 | |
| 8 | Standard BGP 4 ng/ml | 4970 | | 4408 | | |
| 9 | Standard BGP 16 ng/ml | 19487 | 19660 | 18925 | 19098 | |
| 10 | Standard BGP 16 ng/ml | 19833 | | 19271 | | |
| 11 | Standard BGP 64 ng/ml | 83474 | 83268 | 82912 | 82706 | |
| 12 | Standard BGP 64 ng/ml | 83061 | | 82499 | | |
| 13 | Unknown specimen A | 2969 | 3115 | 2407 | 2593 | 2.5 |
| 14 | Unknown specimen A | 3340 | | 2778 | | |
| 15 | Unknown specimen B | 7062 | 7112 | 6500 | 6550 | 5.9 |
| 16 | Unknown specimen B | 7162 | | 6600 | | |
| 17 | Unknown specimen C | 16261 | 16364 | 15699 | 15802 | 13.4 |
| 18 | Unknown specimen C | 16466 | | 15904 | | |

The meanings of abbreviations in Table 3 are as follows:
Total count: count (cpm) of $^{125}$I-labelled anti-BGP monoclonal antibody added into each assay tube.
B-Bo: count (cpm) of anti-BGP monoclonal antibody B complex bound by insolubilized monoclonal antibody A.

We claim:

1. A method for preparing Gla$^{17}$ human osteocalcin and Glu$^{17}$ human osteocalcin or salts thereof by the solid-phase peptide synthetic method, which comprises introducing γ-carboxyglutamic acid into the amino acid sequence of said osteocalcin by employing a protected L-γ-carboxyglutamic acid represented by the formula:

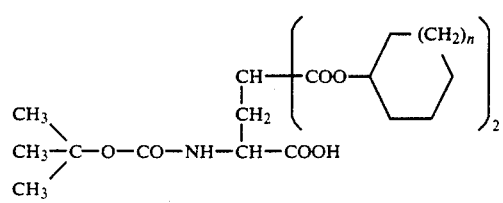

wherein n represents 0, 1 or 2, or a salt thereof in the appropriate position in the reacting sequence of amino acids which form the osteocalcin.

2. The process for preparing human osteocalcin according to claim 1, wherein said Gla[17] human osteocalcin and Glu[17] human osteocalcin have the following chemical formulae:

```
  1                      5                        10
Tyr—Leu—Tyr—Gln—Trp—Leu—Gly—Ala—Pro—Val—Pro—

15                    20
Tyr—Pro—Asp—Pro—Leu—Gla—Pro—Arg—Arg—Gla—Val—

25
     ┌─────────────────────────┐ 30
Cys—Gla—Leu—Asn—Pro—Asp—Cys—Asp—Glu—Leu—Ala—

35                40
Asp—His—Ile—Gly—Phe—Gln—Glu—Ala—Tyr—Arg—Arg—

45           49
Phe—Tyr—Gly—Pro—Val   and 1                      5                        10
Tyr—Leu—Tyr—Gln—Trp—Leu—Gly—Ala—Pro—Val—Pro—

15                    20
Tyr—Pro—Asp—Pro—Leu—Glu—Pro—Arg—Arg—Gla—

25
     ┌─────────────────────────┐ 30
Val—Cys—Gla—Leu—Asn—Pro—Asp—Cys—Asp—Glu—Leu—

35                40
Ala—Asp—His—Ile—Gly—Phe—Gln—Glu—Ala—Tyr—Arg—

45           49
Arg—Phe—Tyr—Gly—Pro—Val.   respectively.
```

3. The process for preparing human osteocalcin according to claim 1, wherein said salt of Gla[17] human osteocalcin or Glu[17] human osteocalcin is a salt of an alkali metal, an alkaline earth metal or an organic base.

4. The process for preparing human osteocalcin according to claim 3, wherein said salt is selected from the group consisting of sodium salt, potassium salt, lithium salt, calcium salt, magnesium salt, a salt of methylamine, ethylamine, diethylamine, triethylamine, benzylamine, pyrrolidine, piperidine, cyclohexylamine, dicyclohexylamine, ethanolamine, diethanolamine, ornithine, lysine and arginine.

5. The process for preparing human osteocalcin according to claim 1, wherein said solid phase method comprises binding valine at the C-terminal amino acid of a desired human osteocalcin to an insoluble resin as a protected amino acid; binding a protected amino acid successively from the C-terminal to form a protected peptide chain; treating said protected peptide chain with a reagent which eliminates side chain protective groups of the respective amino acids; eliminating side chain protective groups of the respective amino acids to give a peptide with the mercapto group of Cys being deprotected; oxidizing the peptide in a buffer to form an intramolecular disulfide bond to obtain a crude human osteocalcin; and then purifying the crude human osteocalcin.

6. The process for preparing human osteocalcin according to claim 5, wherein said insoluble resin is selected from the group consisting of a chloromethyl resin, an oxymethyl resin and a 4-(oxymethyl)-phenylacetamidomethyl resin.

7. The process for preparing human osteocalcin according to claim 6, wherein said protected peptide has the following formula:

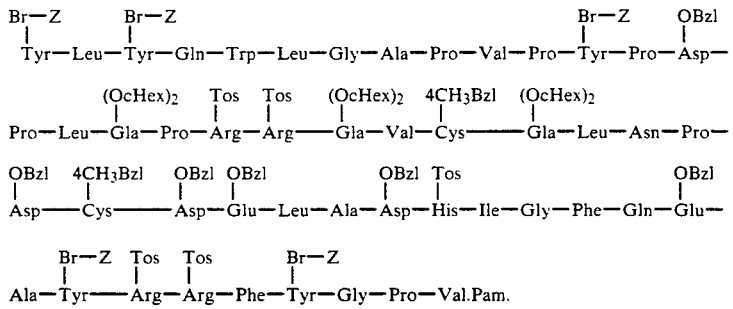

```
Br—Z     Br—Z                              Br—Z   OBzl
 |        |                                 |      |
Tyr—Leu—Tyr—Gln—Trp—Leu—Gly—Ala—Pro—Val—Pro—Tyr—Pro—Asp—

(OcHex)2  Tos Tos   (OcHex)2  4CH3Bzl  (OcHex)2
         |       |   |       |        |         |
Pro—Leu—Gla—Pro—Arg—Arg——Gla—Val—Cys———Gla—Leu—Asn—Pro—

OBzl 4CH3Bzl  OBzl OBzl         OBzl Tos             OBzl
 |     |       |    |            |    |               |
Asp———Cys———Asp—Glu—Leu—Ala—Asp—His—Ile—Gly—Phe—Gln—Glu—

Br—Z  Tos Tos    Br—Z
     |     |   |      |
Ala—Tyr———Arg—Arg—Phe—Tyr—Gly—Pro—Val.Pam.
```

8. The process for preparing human osteocalcin according to claim 5, wherein the reaction of oxidizing the peptide in buffer is carried out by dissolving a crude human osteocalcin with mercapto group of Cys being deprotected in a buffer at an osteocalcin concentration of $10^{-3}$ to $10^{-7}$ mole/liter, adjusting pH to 6.0 to 8.5 and then stirring the solution at 4° to 50° C. for 4 to 30 hours.

9. The process for preparing human osteocalcin according to claim 2, wherein purification is carried out by extraction, recrystallization, gel filtration chromatography, ion exchange chromatography, partition chromatography, adsorption chromatography, reverse phase chromatography, electrophoresis or countercurrent partition.

* * * * *

UNITED STATES PATENT AND TRADEMARK OFFICE
CERTIFICATE OF CORRECTION

PATENT NO. : 5,164,483
DATED : November 17, 1992
INVENTOR(S) : TAKASHI KURIHARA ET AL It is certified that error appears in the above-identified patent and that said Letters Patent is hereby corrected as shown below:

| COL. | LINE |
|---|---|
| 2, | 10, delete "$Glu^7$" and insert --$Glu^{17}$--; |
| 2, | 12, delete "$Gla^7$" and insert --$Gla^{17}$--; |
| 2, | 50, delete "$Gla^7$" and insert --$Gla^{17}$--; |
| 2, | 51, delete, "$Glu^7$" and insert --$Glu^{17}$--; |
| 2, | 54, delete "$Gla^7$" and insert --$Gla^{17}$--; |
| 2, | 54, delete "$Glu^7$" and insert --$Glu^{17}$--; |
| 3, | 49, delete "$Gla^7$" and insert --$Gla^{17}$--; |
| 3, | 52, delete "$Glu^7$" and insert --$Glu^{17}$--; |
| 3, | 56, delete "$Gla^7$" and insert --$Gla^{17}$--; |

UNITED STATES PATENT AND TRADEMARK OFFICE
CERTIFICATE OF CORRECTION

PATENT NO. : 5,164,483
DATED : November 17, 1992
INVENTOR(S) : TAKASHI KURIHARA ET AL It is certified that error appears in the above-indentified patent and that said Letters Patent is hereby corrected as shown below:

COL. LINE

3, 57, delete "$Glu^7$" and insert --$Glu^{17}$--;

4, 20, delete "$Gla^7$" and insert --$Gla^{17}$--;

4, 64, delete "$Gla^7$" and insert --$Gla^{17}$--;

4, 65, delete "$Glu^7$" and insert --$Glu^{17}$--.

Signed and Sealed this

Thirty-first Day of May, 1994

Attest:

BRUCE LEHMAN

*Attesting Officer*   *Commissioner of Patents and Trademarks*